United States Patent [19]

Van Der AA et al.

[11] Patent Number: 4,964,150
[45] Date of Patent: Oct. 16, 1990

[54] DIAGNOSTIC X-RAY EXAMINATION APPARATUS

[75] Inventors: Antonius G. Van Der AA; Theodorus J. M. Van Genechten, both of Eindoven, Netherlands

[73] Assignee: U.S. Philips Corporation, New York, N.Y.

[21] Appl. No.: 459,049

[22] Filed: Dec. 29, 1989

[30] Foreign Application Priority Data

Jan. 6, 1989 [NL] Netherlands .................. 8900028

[51] Int. Cl.⁵ .............................................. H05G 1/02
[52] U.S. Cl. ..................................... 378/197; 378/193
[58] Field of Search ............... 378/195, 196, 197, 198, 378/26, 27

[56] References Cited

U.S. PATENT DOCUMENTS 3,770,955  11/1973  Tomita et al. ........................ 378/197
3,892,967  7/1975   Grady et al. ......................... 378/197
4,591,122  5/1986   Kreuzer .

FOREIGN PATENT DOCUMENTS 3416823  12/1984  Fed. Rep. of Germany .

*Primary Examiner*—Craig E. Church
*Attorney, Agent, or Firm*—William Squire

[57] ABSTRACT

An adjustable X-ray examination apparatus comprises an auxiliary force element, for example, a weight or a resilient element in order to reduce varying counter-forces occurring in a drive mechanism thereof, which auxiliary force element exerts a force which increases in the course of the adjustment. The force acts notably with a moment which increases towards the extreme zone of an adjustment. The auxiliary force element may be mounted and adjusted so that a substantially constant external force suffices for a full range of adjustment of the X-ray examination apparatus.

6 Claims, 1 Drawing Sheet

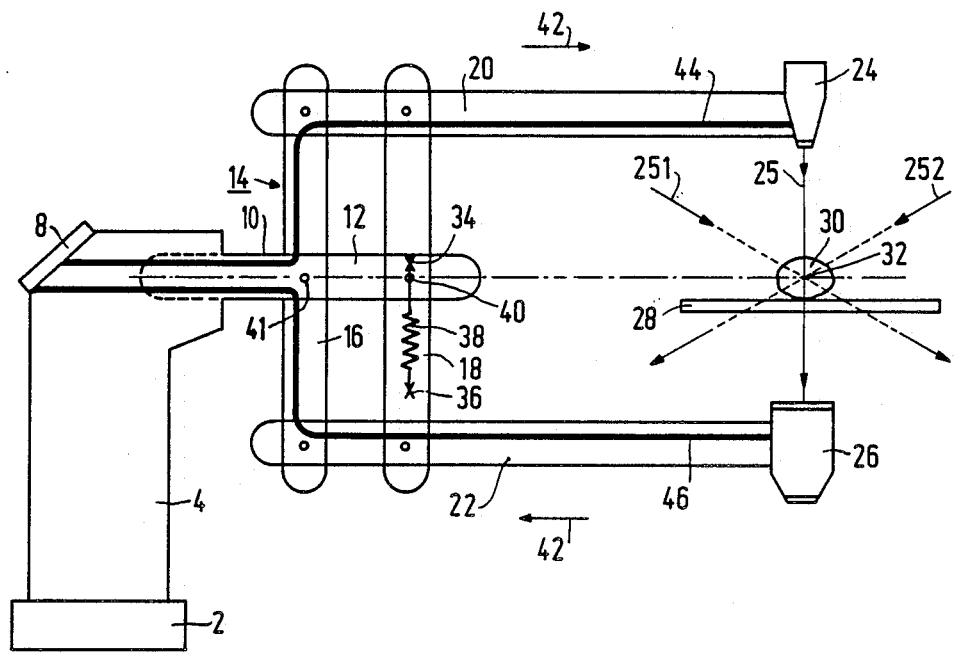

DIAGNOSTIC X-RAY EXAMINATION APPARATUS

The invention relates to an X-ray examination apparatus, comprising a supporting shaft and a holder which comprises two side arms and two transverse arms which are pivotably interconnected so as to form a parallelogram, the transverse arms intersecting the supporting shaft and being connected to the supporting shaft so as to be rotatable about a respective rotary shaft extending transversely of the supporting shaft, an X-ray source and X-ray detector being secured to opposite ends of the side arms so as to face one another.

An X-ray examination apparatus of this kind is known from U.S. No. 3,892,967.

An apparatus described therein has the drawback that during various adjustment movements of the holder a comparatively high counterforce must be overcome in the drive mechanism of the holder, notably in order to reach extreme positions with respect to an object to be irradiated. Notably for angular adjustment, achieved by rotation of the transverse arms about the rotary shafts, the counterforces may become comparatively high. The counterforce is caused inter alia by friction in the drive mechanism of the holder, but notably by deformation and/or displacement of leads accommodated therein, for example for the X-ray source and the X-ray detector.

It is an object of the invention to mitigate this drawback; to achieve this, an apparatus of the kind set forth in accordance with the invention is characteriZed in that the X-ray examination apparatus includes an auxiliary force element for storing potential energy upon rotation of the transverse arms in a first direction of rotation and for delivering the potential energy to the X-ray examination apparatus upon rotation of the transverse arms in a second direction of rotation.

Because an auxiliary force element, such as a pulling mass or a resilient element, in an apparatus in accordance with the invention at least partly compensates for the counterforce, varying over an adjusting range, by delivering the previously stored potential energy, the adjusting force which is usually to be delivered by hand is substantially reduced, notably in cases where such force would be greatest in the absence of a compensating element. Because the adjusting force to be externally applied is reduced, the adjustment of any safety stops can be more sensitive and the force to be applied can be more homogeneous over an entire range.

It is to be noted that U.S. No. 3,770,955 discloses an X-ray examination apparatus which comprises a parallelogram-shaped holder with two transverse arms, each of which is rotatable about a rotary shaft. The rotation of the transverse arms is realized by a hydraulic system which comprises a cylinder, one end of which is connected to one of the transverse arms. The hydraulic system delivers the work required for rotation of the transverse arms to the X-ray apparatus and clearly constitutes a principal force element and not an auxiliary force element. No potential energy is stored in the cylinder 18. The cited Patent Specification does not disclose that the cylinder 18 must deliver a force which varies along a displacement path of the holder and that this problem can be solved by using an auxiliary force element.

An embodiment of an X-ray examination apparatus in accordance with the invention is characterized in that the auxiliary force element delivers the potential energy as a force which presses the transverse arms in the second direction of rotation and exhibits an extreme value in a perpendicular position of the transverse arms and the supporting shaft.

It has been found that the rotation of the transverse arms about the rotary shafts requires a force which, for a first direction of rotation, for example from a position in which the transverse arms enclose an angle of 90° with respect to the supporting shaft to a position where the transverse arms extend substantially parallel to the supporting shaft, deviates from the force required for backrotation in a direction of rotation which opposes the first direction of rotation. By storing upon rotation in the direction of rotation requiring the lowest force, at least a part of the applied force as potential energy in the auxiliary force element said potential energy being released again upon backrotation of the transverse arms as a force which rotates the transverse arms back again, the externally applied force for backrotation may be comparatively small and constant. The force exerted on the transverse arms by the auxiliary force element is not constant but has a maximum value in one of the extreme positions of the transverse arms, that is to say a position in which an angle enclosed with respect to the supporting shaft amounts to 90° or a position in which this angle is comparatively small. A constant external force has the advantage that the manual adjustment of the X-ray examination apparatus can be realized in an attractive manner and also enables sensitive adjustment of any protection devices in the drive mechanism.

Preferably, the auxiliary force element is formed by a resilient element having a moment which is adjustable with respect to the rotary shafts, so that the auxiliary force element occupies only little space and can be readily integrated in an X-ray examination apparatus.

Some preferred embodiments in accordance with the invention will be described in detail hereinafter with reference to the drawing.

The sole FIGURE of the drawing shows an X-ray examination apparatus, comprising a column 4 which is arranged on a base 2, a control panel 8 and a rotary supporting shaft 10 being arranged on an upper part 6 of said column. A free end 12 of the supporting shaft 10 supports a parallelogram-shaped holder 14 with a first transverse arm 16, a second transverse arm 18, a first side arm 20 and a second side arm 22. The transverse arms 16 and 18 are rotatable about rotary shafts 40 and 41.

An X-ray source 24 and an X-ray detector 26 are accommodated at free ends of the side arms 20 and 22. A radiation vector 25 which emanates from the X-ray source 24, preferably an X-ray tube, irradiates an object 30 arranged on a supporting table 28 and is incident on the X-ray detector 26, for example an X-ray image intensifier tube or an X-ray film cassette.

Using the parallelogram-shaped holder 14, an angulation can be imparted to the radiation vector 25 by rotation of the transverse arms 16 and 18, which angulation covers a range as denoted by the radiation vector directions 251 and 252. The radiation vector 25 customarily extends through an isocentre 32 which is situated substantially centrally within the object to be examined, and the extreme directions 251 and 252 enclose an angle of, for example 120°. For further adjustments and facilities of such an apparatus, reference is made to the cited U.S. No. 3,892,967.

A tension spring 38 is arranged between points of attachment 34 and 36 in the apparatus shown. A connecting line between the points of attachment 34 and 36 intersects the rotary shaft 40. When the spring is mounted in the tensioned condition, upon rotation of the transverse arms 16 and 18 the tensile force will increase, the side arms 20 and 22 being displaced in the direction denoted by arrows 42. With respect to the rotary shaft 40 the tensile force forms a moment which increases as the rotation of the transverse arms 16 and 18 increases. For backrotation of the transverse arms 16 and 18, during which the side arms 20 and 22 move in the direction opposing that of the arrows 42, less external force will be required because of the appearance of this moment. The moment is maximum when an angle enclosed by the transverse arms 16 and 18 with respect to the supporting shaft 10 is smallest. Using a compression spring, for example a gas spring, a similar effect can be realized by situating the point of attachment 34 below the point of rotation 40, viewed in the drawing. When the tension spring 38 is replaced by a pressure spring, an opposite force is obtained which is maximum when the angle between the transverse arms 16 and 18 and the supporting shaft 10 is approximately 90°. Other points of attachment are, for example, two diagonally oppositely situated pivots in the parallelogram-shaped support 14, or opposite parallel sides of the support 14. By choosing the distance between the point of attachment 34 and the rotary shaft 40 and by adjusting the pressure force or the tensile force of the spring 38, the active force to be delivered by the spring can be optimized over the adjusting range. In a practical embodiment, the resilient element can be accommodated in a parallelogram arm which is usually constructed as a pipe.

The counterforce of the drive mechanism is delivered mainly by compression or in any case deformation of leads 44 and 46 for the X-ray source 24 and the X-ray detector 2, respectively, in the present embodiment. These leads are preferably mounted so that they closely adjoin the drive mechanism in order to prevent disturbing loops. By compensating the forces occurring due to the deformation of the leads, if desirable, the leads can be mounted so as to comprise even smaller loops for motion and can be arranged, if desired, in hollow spaces of the system of arms of the drive mechanism. By utilizing an adjustable spring element which is mounted so that the element is tensioned, via an external force, in a first part of an adjusting range, the energy thus stored being used for compensating the counterforce in the extreme zones of the range, an adjustment can be realized so that the external force to be applied is substantially constant throughout an adjusting range. The constant force can still be substantially lower than the maximum force otherwise required in the extreme zones of the adjusting range.

Similarly, using a weight, a moment can be realized which increases as the angulation angle increases. An auxiliary force in accordance with the invention can also be used for other adjustments where an increasing counterforce is experienced, for example the rotation of a C-arm and the like.

What is claimed is:

1. An X-ray examination apparatus, comprising a supporting shaft and a holder which comprises two side arms and two transverse arms which are pivotably interconnected so as to form a parallelogram, the transverse arms intersecting the supporting shaft and being connected to the supporting shaft so as to be rotatable about a respective rotary shaft extending transversely of the supporting shaft, an X-ray source and an X-ray detector being secured to opposite ends of the side arms so as to face one another, characterized in that an auxiliary force element is included secured to at least one of said arms for storing potential energy upon rotation of the transverse arms in a first direction of rotation and for delivering the potential energy to said at least one arm upon rotation of the transverse arms in a second direction of rotation.

2. An X-ray examination apparatus as claimed in claim 1, characterized in that the auxiliary force element includes means arranged so as to deliver the potential energy as a force which presses the transverse arms in the second direction of rotation and exhibits an extreme value in a perpendicular position of the transverse arms to the supporting shaft.

3. An X-ray examination apparatus as claimed in claim 2, characterized in that means are included for adjusting the force.

4. An X-ray examination apparatus as claimed in claim 1, characterized in that the auxiliary force element comprises a resilient element.

5. An X-ray examination apparatus as claimed in claim 4, characterized in that the resilient element is secured to the holder in two points of attachment which are situated on opposing sides of the supporting shaft.

6. An X-ray examination apparatus as claimed in claim 5, characterized in that the first point of attachment is situated on one of the transverse arms, the second point of attachment being situated on the supporting shaft.

* * * * *